(12) United States Patent
Wu et al.

(10) Patent No.: US 8,358,408 B2
(45) Date of Patent: Jan. 22, 2013

(54) APPARATUS FOR PERFORMING SERS

(75) Inventors: Wei Wu, Palo Alto, CA (US); Min Hu, Sunnyvale, CA (US); Fung Suong Ou, Palo Alto, CA (US); Zhiyong Li, Redwood City, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 265 days.

(21) Appl. No.: 12/771,824

(22) Filed: Apr. 30, 2010

(65) Prior Publication Data

US 2011/0267609 A1 Nov. 3, 2011

(51) Int. Cl.
*G01J 3/44* (2006.01)

(52) U.S. Cl. ........................................ 356/301

(58) Field of Classification Search .............. 356/72–73, 356/301

See application file for complete search history.

(56) References Cited

U.S. PATENT DOCUMENTS

| | | | |
|---|---|---|---|
| 7,224,451 B2 | 5/2007 | Naya | |
| 7,288,419 B2 | 10/2007 | Naya | |
| 7,351,588 B2 | 4/2008 | Poponin | |
| 7,476,787 B2 * | 1/2009 | Thomas et al. | 250/306 |
| 7,576,854 B2 | 8/2009 | Wang et al. | |
| 7,586,601 B2 | 9/2009 | Ebstein | |
| 7,609,378 B2 | 10/2009 | Konakahara | |
| 7,651,863 B2 | 1/2010 | Hulteen | |
| 7,656,525 B2 | 2/2010 | Zhao et al. | |
| 7,707,647 B2 | 4/2010 | Konakahara | |
| 2001/0006869 A1 * | 7/2001 | Okamoto et al. | 445/51 |
| 2004/0135997 A1 | 7/2004 | Chan et al. | |
| 2006/0250613 A1 | 11/2006 | Demuth et al. | |
| 2007/0015288 A1 | 1/2007 | Hulteen et al. | |
| 2007/0086001 A1 | 4/2007 | Islam | |
| 2007/0115469 A1 | 5/2007 | Ebstein | |
| 2008/0079104 A1 * | 4/2008 | Stewart et al. | 257/433 |
| 2009/0033929 A1 | 2/2009 | Mazur et al. | |
| 2009/0117646 A1 | 5/2009 | Stordeur et al. | |
| 2010/0062226 A1 | 3/2010 | Hulteen et al. | |
| 2010/0109203 A1 | 5/2010 | Chen et al. | |
| 2010/0321684 A1 | 12/2010 | Bratkovski | |
| 2011/0128536 A1 | 6/2011 | Bond et al. | |
| 2012/0013903 A1 | 1/2012 | Kuo | |
| 2012/0113419 A1 | 5/2012 | Wang | |
| 2012/0161600 A1 | 6/2012 | Norris et al. | |

FOREIGN PATENT DOCUMENTS

| | | |
|---|---|---|
| WO | WO 2006/138442 A2 | 12/2006 |
| WO | PCT/US2009/52308 | 7/2009 |
| WO | WO 2009/117646 | 9/2009 |
| WO | WO 2010/056258 | 5/2010 |

OTHER PUBLICATIONS

Linyou Cao et al., "Enhance Raman Scattering from Individual Semiconductor Nanocones and Nanowires", Physical Review Letters PRL 96, 157402, 2006.

Schmidt at al., "Towards Easily Reproducible Nano-Structured SERS Substrates", IEEE Sensors 2009 Conference, pp. 1763-1767.

Wu et al., "One-Kilobit Cross-Bar Memory Circuits at 30-nm Half-Pitch Fabricated by Nanoimprint Lithography", Springer-Verlag, Pub online Mar. 11, 2005, pp. 1173-1178.

(Continued)

*Primary Examiner* — Tarifur Chowdhury
*Assistant Examiner* — Abdullahi Nur (57) ABSTRACT

An apparatus for performing Surface Enhanced Raman Spectroscopy (SERS) includes a reflective layer positioned above the substrate, a plurality of tapered nanowires disposed above the reflective layer, each of the plurality of tapered nanowires having a tapered end directed away from the reflective layer.

20 Claims, 9 Drawing Sheets

OTHER PUBLICATIONS

Hu et al., "Metal Coated Si Nanograss as Highly Sensitive SERS Sensors" Proc. of SPIE, vol. 7312, pp. 73120I-1-6.
Gilles et al., "UV Nanoimprint Lithography with Rigid Polymer Molds", Microelectronic Engineering 86 (2009), pp. 661-664.
He et al., "Large-Scale Synthetic of Flexible Free-Standing SERS Substrates with High Sensitivity:Electrospun PVA Nanofibers Embedded with Cntrolled Alignment of Silver-Nanoparticles", ACSNANO, vol. 3, No. 12, published online Nov. 23, 2009.
PCT Search Report, PCT/US2008/083827.
PCT Search Report, PCT/US2009/052308.

* cited by examiner

APPARATUS FOR PERFORMING SERS

GOVERNMENT LICENSE RIGHTS

This invention was made in the course of research partially supported by grants from the U.S. Government. The U.S. Government has certain rights in the invention.

CROSS-REFERENCE TO RELATED APPLICATIONS

The present application is related to PCT Application Serial No. PCT/US08/83827, filed on Nov. 17, 2008, and entitled "A SUBSTRATE FOR SURFACE ENHANCED RAMAN SCATTERING (SERS)"; PCT Application Serial No. PCT/US09/52308, filed on Jul. 30, 2009, and entitled "NANOWIRE-BASED SYSTEMS FOR PERFORMING RAMAN SPECTROSCOPY"; U.S. patent application Ser. No. 12/771,440, filed on Apr. 30, 2010, and entitled "SURFACE-ENHANCED RAMAN SPECTROSCOPY DEVICE AND A MOLD FOR CREATING AND A METHOD FOR MAKING THE SAME"; and U.S. patent application Ser. No. 12/771,753, filed on Apr. 30, 2010 and entitled "ENHANCING SIGNALS IN SURFACE ENHANCED RAMAN SPECTROSCOPY (SERS)", the disclosures of which are hereby incorporated by reference in their entireties.

BACKGROUND

Raman spectroscopy is a spectroscopic technique used in condensed matter physics and chemistry to study vibrational, rotational, and other low-frequency modes in molecular systems. In a Raman spectroscopic experiment, a monochromatic beam of light of a particular wavelength range passes through a sample of molecules and a spectrum of scattered light is emitted. The term "light" is not limited to electromagnetic radiation with wavelengths that lie in the visible portion of the electromagnetic spectrum but also includes electromagnetic radiation with wavelengths outside the visible portion, such as the infrared and ultraviolet portions of the electromagnetic spectrum, and can be used to refer to both classical and quantum electromagnetic radiation. The spectrum of wavelengths emitted from the molecule is called a "Raman spectrum" and the emitted light is called "Raman scattered light." A Raman spectrum can reveal electronic, vibrational, and rotational energies levels of a molecule. Different molecules produce different Raman spectrums that can be used like a fingerprint to identify molecules and even determine the structure of molecules.

The Raman scattered light generated by a compound (or ion) adsorbed on or within a few nanometers of a structured metal surface can be 103-106 times greater than the Raman scattered light generated by the same compound in solution or in the gas phase. This process of analyzing a compound is called surface-enhanced Raman spectroscopy ("SERS"). In recent years, SERS has emerged as a routine and powerful tool for investigating molecular structures and characterizing interfacial and thin-film systems, and even enables single-molecule detection. Engineers, physicists, and chemists continue to seek improvements in systems and methods for performing SERS.

BRIEF DESCRIPTION OF THE DRAWINGS

Embodiments are illustrated by way of example and not limited in the following figure(s), in which like numerals indicate like elements, in which.

DETAILED DESCRIPTION

For simplicity and illustrative purposes, the principles of the embodiments are described by referring mainly to examples thereof. In the following description, numerous specific details are set forth in order to provide a thorough understanding of the embodiments. It will be apparent however, to one of ordinary skill in the art, that the embodiments may be practiced without limitation to these specific details. In other instances, well known methods and structures are not described in detail so as not to unnecessarily obscure the description of the embodiments.

Embodiments of the present invention are directed to nanowire-based systems for performing surface-enhanced Raman spectroscopy. The systems include an array of tapered nanowires disposed above a reflective layer configured to reflect light toward the tips of the tapered nanowires and thereby enhance performance of Raman spectroscopy at the tips. In addition, SERS-active nanoparticles are disposed on the outer surface of the tapered nanowires and, in certain embodiments, near the tapered ends, or tips, of the tapered nanowires. With optical pumping, the nanowires emit Raman excitation light. In this regard, the tapered nanowires and the reflective layer are configured to direct a substantial portion of the Raman excitation light emitted from an external light source toward the tapered ends of the nanowires to interact with the SERS-active nanoparticles and enhance the Raman spectrum of molecules disposed on or near the SERS-active nanoparticles.

I. Optically Operated SERS-Active Systems

Figure 1A:
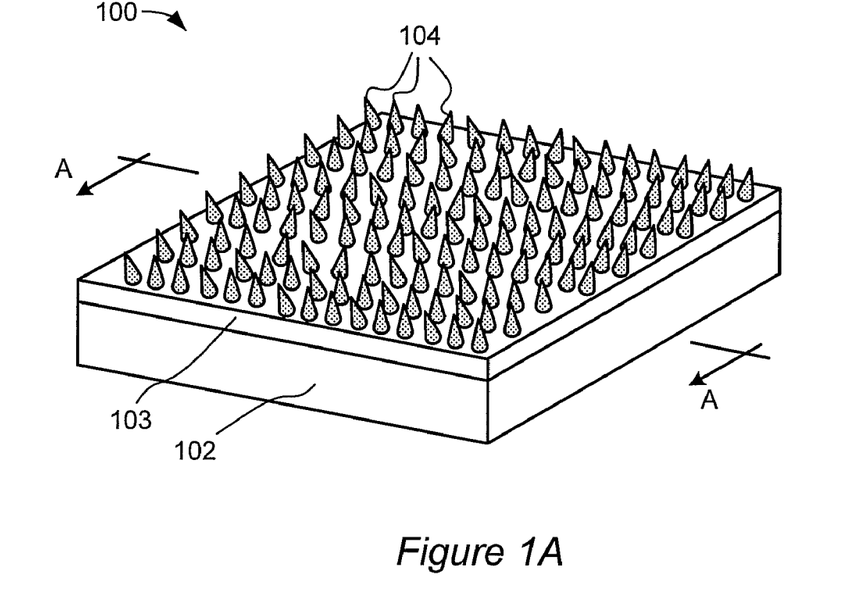
FIG. 1A shows an isometric view of a SERS-active apparatus, according to an embodiment of the invention.

FIG. 1A shows an isometric view of a SERS-active apparatus 100 configured in accordance with embodiments of the present invention. It should be understood that the apparatus 100 depicted in FIG. 1 may include additional components and that some of the components described herein may be removed and/or modified without departing from a scope of the apparatus 100. It should also be understood that the components depicted in FIG. 1 are not drawn to scale and thus, the components may have different relative sizes with respect to each other than as shown therein.

The apparatus 100 includes a substrate 102 and a reflective layer 103 disposed above a surface of the substrate 102. The apparatus 100 also includes a plurality of tapered nanowires 104 disposed above the reflective layer 103. As shown in the example of FIG. 1A, the nanowires 104 are configured to taper away from the substrate 102 and the reflective layer 103. In addition, the nanowires 104 are depicted as being randomly distributed, but may also be arranged in a predetermined configuration to therefore distribute the tapered nanowires 104 in a substantially uniform density. Furthermore, the nanowires 104 may be shaped as, pillars, pyramids, cones, hemispheres, etc., or amorphous shapes.

Figure 1B:
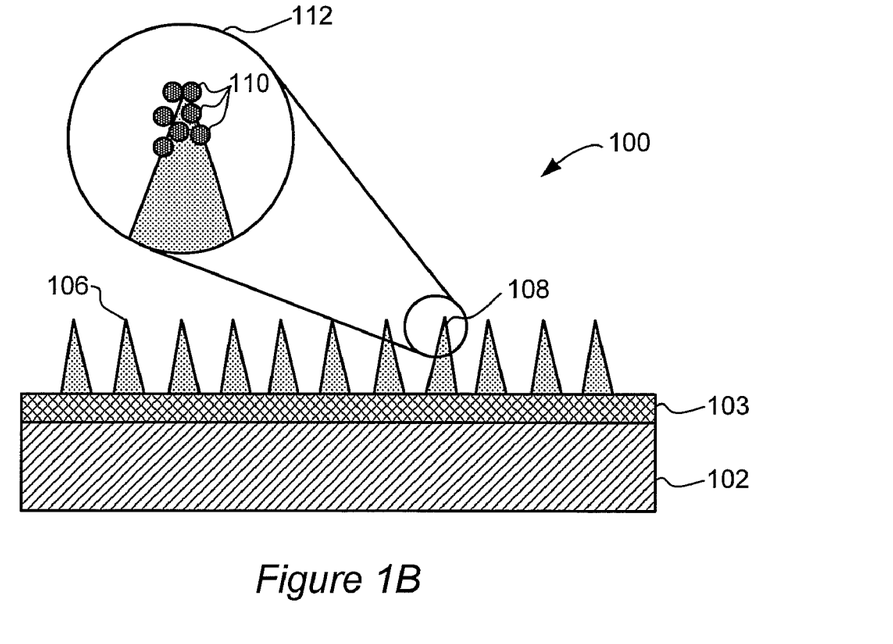
FIGS. 1B and 1C, respectively, show cross-sectional views along a line A-A, shown in FIG. 1A of the SERS-active apparatus, according to embodiments of the invention.
Figure 1C:
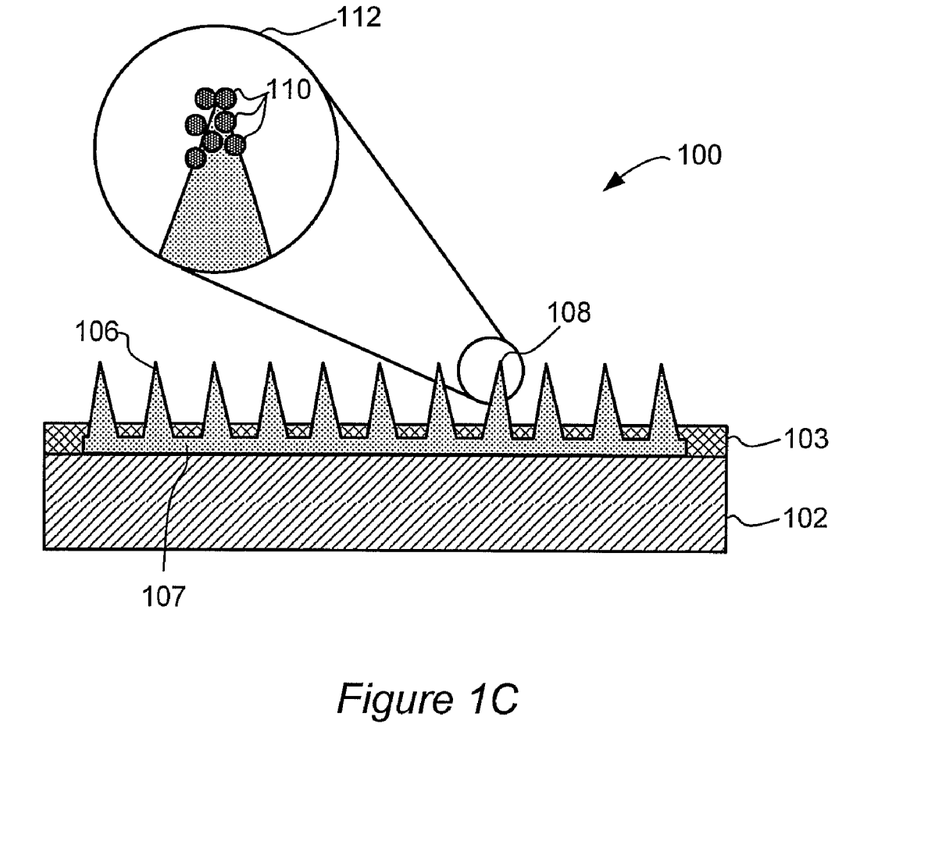

FIGS. 1B and 1C, respectively, show cross-sectional views along a line A-A, shown in FIG. 1A, of the apparatus 100, in accordance with embodiments of the present invention. In the examples of FIGS. 1B and 1C, the tapered nanowires 104 may have a symmetric, inverted-cone shape, such as tapered nanowire 106, or an asymmetric, inverted-cone shape, such as tapered nanowire 108. The apparatus 100 also includes SERS-active nanoparticles 110 disposed near the tapered end, or tip, of the nanowires. In FIGS. 1B and 1C, the tapered end of nanowire 108 is magnified in an enlargement 112 revealing a plurality of SERS-active nanoparticles 110 disposed on the outer surface, near the tip, of the nanowire 108. Note that embodiments of the present invention are not limited to nanoparticles disposed over just the tip of the nanowires. In other embodiments, the nanoparticles can be disposed over nearly the entire surface of the nanowires.

The substrate 102 may be composed of a dielectric material, including glass, $SiO_2$, $Al_2O_3$, or any other suitable material, such as a metal or semiconductor. The reflective layer 103 may be composed of a reflective metallic or other type of reflective material and may be fabricated to have a mirror-like functionality. In addition, the reflective layer 103 may be fabricated to have a relatively flat, concave, convex, or amorphous surface.

As shown in FIG. 1B, the reflective layer 103 is disposed directly on a surface of the substrate 102. In accordance with one embodiment, the substrate 102 and the reflective layer 103 may be formed as a common layer. In this regard, the substrate 102 may be formed to include either a single reflective surface or the entire substrate 102 may be formed and finished to be reflective. As shown in FIG. 1C, the tapered nanowires are connected to each other by a connecting element 107, which may be, for instance, a by-product of the nanowire formation process. In this example, the reflective layer 103 is disposed on top of the connecting element 107, substantially between the tapered nanowires.

The tapered nanowires 104 may be composed of materials enabling the nanowires to be operated as gain media when the SERS-active system 100 is optically pumped. For example, the nanowires may be composed of a direct or an indirect semiconductor material. Direct semiconductors are characterized by the valence band maximum and the conduction band minimum occurring at approximately the same wavenumber. As a result, an electron in the conduction band recombines with an unoccupied electronic state in the valence band giving off the energy difference as a photon of light. In contrast, indirect semiconductors are characterized by the valence band maximum and the conduction band minimum occurring at different wavenumbers. An electron in the conduction band minimum recombines with an unoccupied electronic state in the valence band maximum by first undergoing a momentum change followed by a change in electronic energy.

Indirect and direct semiconductors may be elemental and compound semiconductors. Indirect elemental semiconductors include silicon (Si) and germanium (Ge), and compound semiconductors include III-V materials, where Roman numerals III and V represent elements in the IIIa and Va columns of the Periodic Table of the Elements. Compound semiconductors can be composed of column IIIa elements, such as aluminum (Al), gallium (Ga), and indium (In), in combination with column Va elements, such as nitrogen (N), phosphorus (P), arsenic (As), and antimony (Sb). Compound semiconductors may also be further classified according to the relative quantities of III and V elements. For example, binary semiconductor compounds include GaAs, InP, InAs, and GaP; ternary compound semiconductors include $GaAs_yP_{1-y}$, where y ranges from greater than 0 to less than 1; and quaternary compound semiconductors include $In_xGa_{1-x}As_yP_{1-y}$, where both x and y independently range from greater than 0 to less than 1. Other types of suitable compound semiconductors include II-VI materials, where II and VI represent elements in the IIb and VIa columns of the periodic table. For example, CdSe, ZnSe, ZnS, and ZnO are examples of binary II-VI compound semiconductors.

The tapered nanowires 104 may be formed using a vapor-liquid-solid ("VLS") chemical synthesis process. This method may involve depositing particles of a catalyst material such as gold or titanium on a surface of the substrate 102 or the reflective layer 103. The substrate 102 and the reflective layer 103 may be placed in a chamber and heated to temperatures typically ranging between about 250° C. to about 1000° C. Precursor gasses including elements or compounds that will be used to form the nanowires are introduced into the chamber. The particles of the catalyst material cause the precursor gasses to at least partially decompose into their respective elements, some of which are transported on or through the particles of catalyst material and deposited on the underlying surface. As this process continues, nanowires grow with the catalyst particle remaining on the tip or end of the nanowires. Nanowires may also be formed by physical vapor deposition, by surface atom migration, or etched back by reactive etching with or without a lithographically defined masking pattern.

Figure 2A:
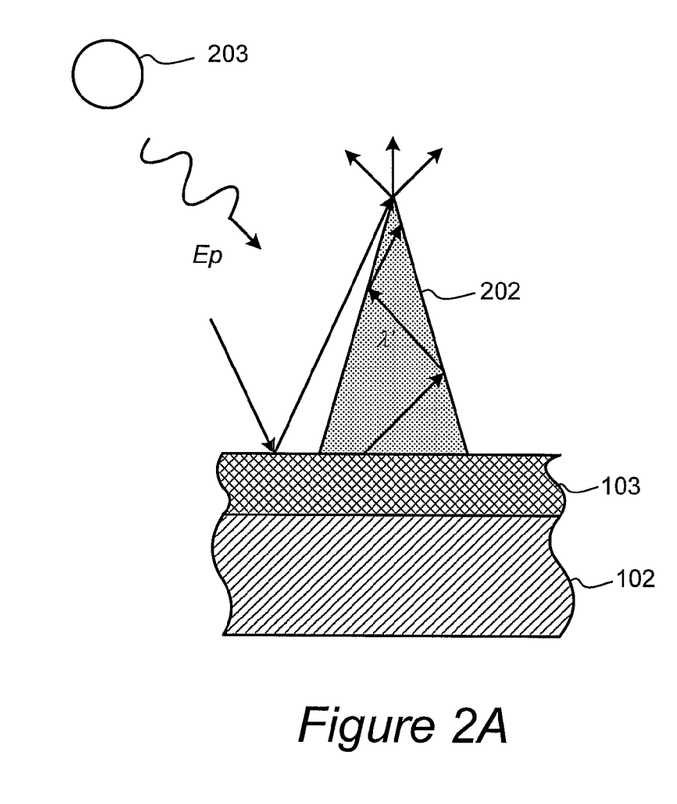
FIG. 2A shows optically pumping a tapered nanowire, according to an embodiment of the invention.

The nanowire material may be selected to emit Raman excitation light with Raman excitation wavelengths, $\lambda'$, that enhance Raman spectrum of molecules located at or near the SERS-active nanoparticles 110 when the nanowires 104 are optically pumped with light of an appropriate pump wavelength $\lambda_p$ from a light source 203 and reflected from the reflective layer 103. FIG. 2A shows optically pumping a tapered nanowire 202 in accordance with embodiments of the present invention. Although FIG. 2A has been depicted as having the configuration depicted in FIG. 1B, it should clearly be understood that FIG. 2A may instead have the configuration depicted in FIG. 1C without departing from a scope of the invention. In FIG. 2A, tapered nanowire 202 is illuminated with light having a pump wavelength λp and corresponding energy Ep:

$$E_p = \frac{hc}{\lambda_p}$$

where h is Planck's constant, and c is the speed of light in free space.

Figure 2B:
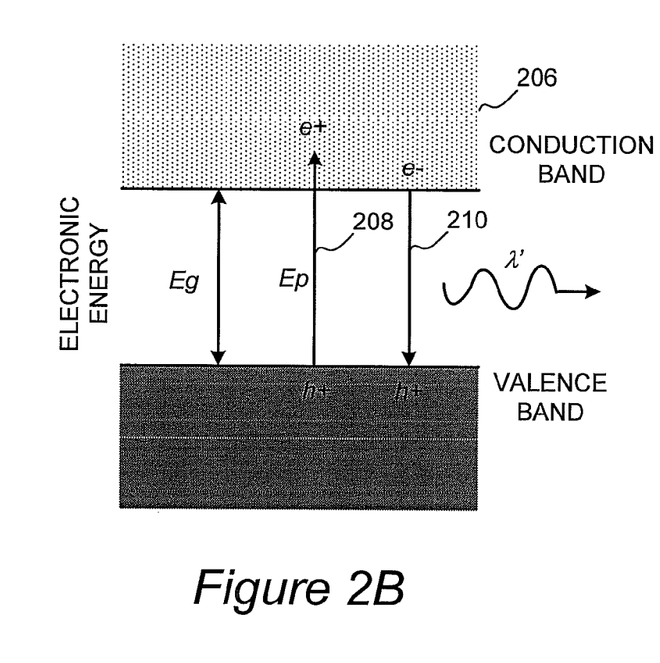
FIG. 2B shows an exemplary electronic energy band diagram associated with a tapered nanowire, according to an embodiment of the invention.

FIG. 2B shows an exemplary electronic energy band diagram associated with a tapered nanowire in accordance with embodiments of the present invention. In FIG. 2B, heavily shaded region 204 represents a mostly filled continuum of electronic energy states and lightly shaded region 206 represents a mostly vacant continuum of unoccupied electronic energy states called "holes" which act like positive charge carriers. Electrons and holes are called "charge carriers." As shown in the example of FIG. 2B, optically pumping a nanowire, such as nanowire 202, with light of photon energy Ep 208 exceeding the band gap energy Eg of the nanowire material (i.e., Ep>Eg), causes electrons (e−) to be excited from near the top of the valence band into electronic energy states in the conduction band, leaving holes (h+) near the top of the valence band. An electron excited into the conduction band may relax via thermal processes to a relatively lower electronic energy state in the conduction band, where the electron remains until the electron spontaneously recombines with a hole in the valence band and emits a photon of light with Raman excitation wavelength λ' and corresponding energy E' 210 satisfying the condition:

$$E_p > E' = \frac{hc}{\lambda'} \geq E_g$$

In other embodiments, the material comprising the tapered nanowires may be doped with impurity atoms that introduce one or more metastable states into the electronic band gap near the bottom of the conduction band from which excited electrons transition to and remain for a short period of time before spontaneously recombining with holes in the valence band. The impurities may be selected to emit Raman excitation light with Raman excitation wavelengths λ'.

Returning to FIG. 2A, the light emitted from the nanowire 202 may be trapped by internal reflection within the nanowire 202 due to the contrast between the refractive index of the nanowire 202 material and the relatively lower refractive index of the surrounding air. As a result, a substantial portion of the emitted light may be reflected off of the interior walls within the nanowire, directed toward the tip of the nanowire, and emitted near the tip of the nanowire, as shown in FIG. 2A. In addition, a substantial portion of the emitted light may be reflected off of the reflective layer 103 and directed toward the tip of the nanowire. The light produced by the spontaneous emission and the reflection may also stimulate the emission of more Raman excitation light, and the stimulated emissions further stimulates the emission of even more Raman excitation light. The light continues to build-up and may constructively interfere to produce amplified light with the Raman excitation wavelengths λ' emitted near the tip of the nanowire 202.

Figure 3A:
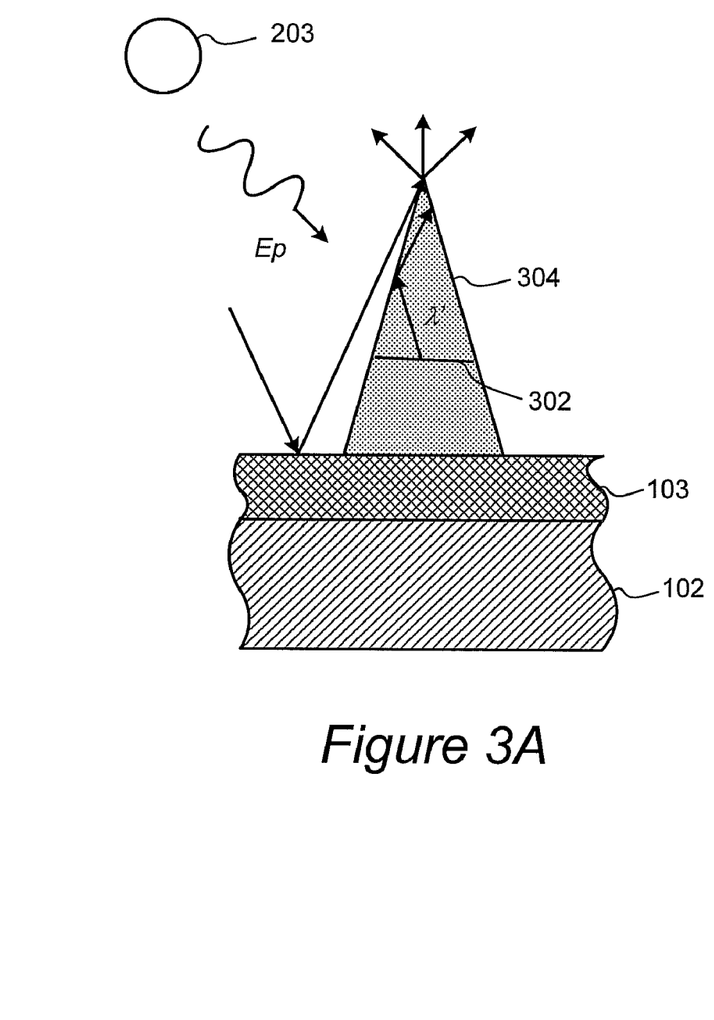
FIG. 3A shows a cross-sectional view of optically pumping a QW embedded in a tapered nanowire, according to an embodiment of the invention.
Figure 3B:
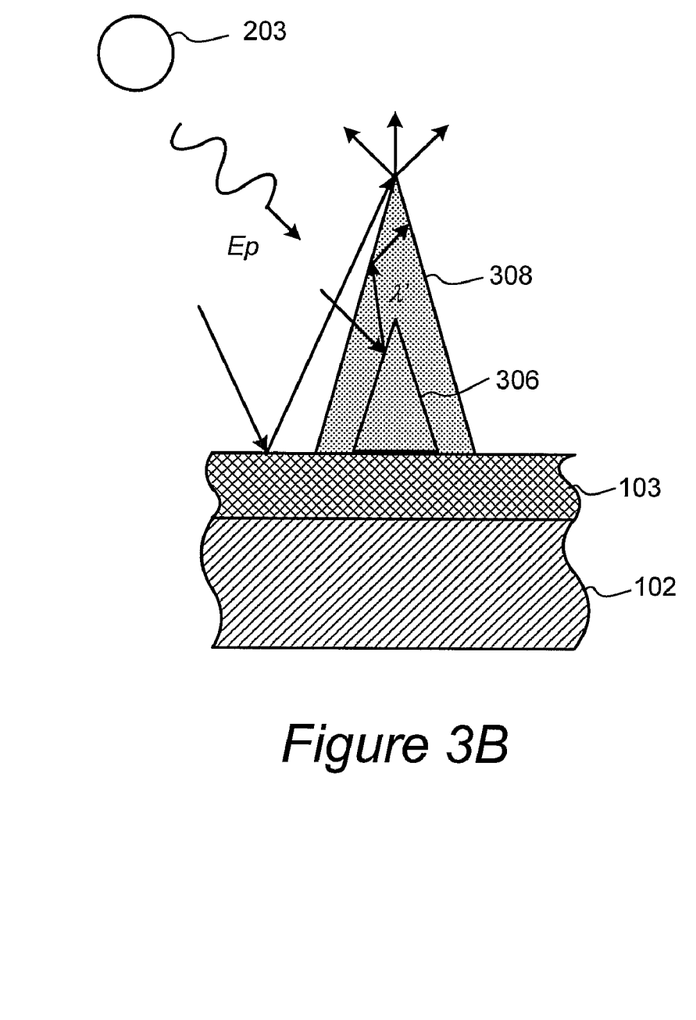
FIG. 3B shows a cross-sectional view of optically pumping a core-shell QW embedded within a tapered nanowire, according to an embodiment of the invention.
Figure 3C:
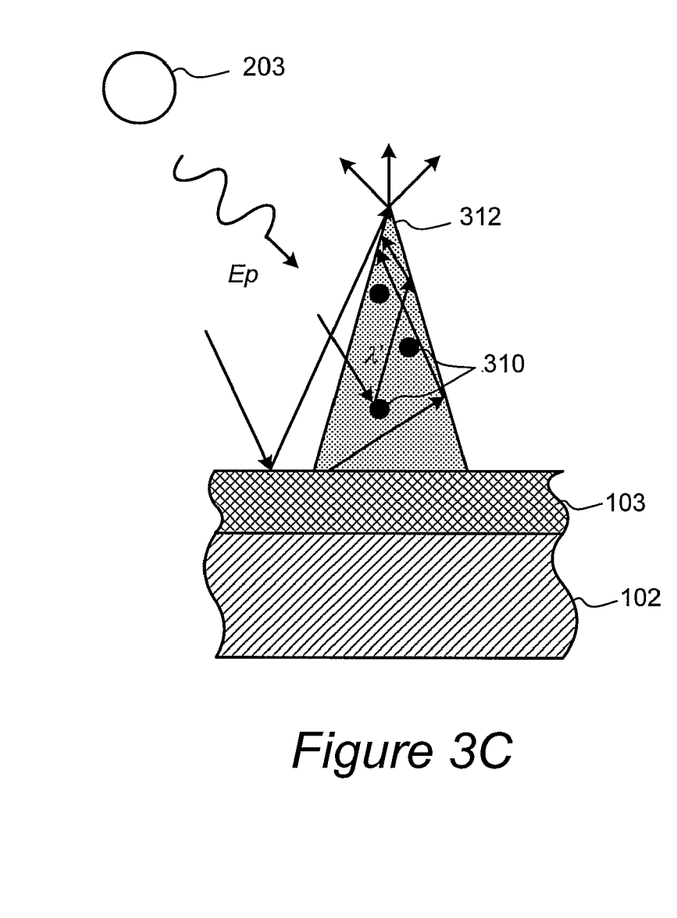
FIG. 3C shows optically pumping light-emitting particles embedded within a tapered nanowire, according to an embodiment of the invention.

In other embodiments, the tapered nanowires may be configured with one or more light emitters, including quantum wells ("QWs") or light-emitting particles, such as quantum dots ("QDs"), atoms or molecules, that can be selected and dimensioned to emit Raman excitation light with Raman excitation wavelengths λ'. FIG. 3A shows a cross-sectional view of optically pumping a QW 302 embedded in a tapered nanowire 304 in accordance with embodiments of the present invention. The QW 302 is a layer oriented substantially parallel to the surface of the substrate 102. FIG. 3B shows a cross-sectional view of optically pumping a core-shell QW 306 embedded within a tapered nanowire 308 in accordance with embodiments of the present invention. In other embodiments, rather than an embedded core-shell QW, as shown in FIG. 3B, the QW can be a shell located on at least a portion of the outer surface of the nanowire 308. FIG. 3C shows optically pumping light-emitting particles 310 embedded within a tapered nanowire 312 in accordance with embodiments of the present invention. Although FIGS. 3A-3C have been depicted as having the configuration depicted in FIG. 1B, it should clearly be understood that FIGS. 3A-3C may instead have the configuration depicted in FIG. 1C without departing from a scope of the invention.

The electronic band gap of QDs and QWs may be determined by the size of the QDs or thickness of the QWs in addition to the type of materials selected for the QDs and QWs. In other words, the Raman excitation wavelength λ' can be obtained by appropriate selection of the size of the QDs, thickness of the QWs, and the QD or QW materials. In certain embodiments, for example, QDs or QW can be composed of GaAs and the remaining tapered nanowire can be composed of AlGaAs; or for example, QDs or QW can be composed of InGaAsP and the remaining tapered nanowire can be composed of InP. The QWs can be unstrained in which the lattice constant for the QWs nearly matches the lattice constant of the remaining nanowire. Examples of unstrained QWs include a GaAs QW that substantially matches the lattice of a $Al_{0.2}Ga_{0.8}As$ bulk material, and the same situation occurs for a $In_{1-x}Ga_xAs_yP_{1-y}$ QW in bulk InP when x≅0.45y. In other embodiments, particular atoms and molecules can be selected for the light-emitting particulars to emit the Raman excitation wavelength λ'.

Figure 3D:
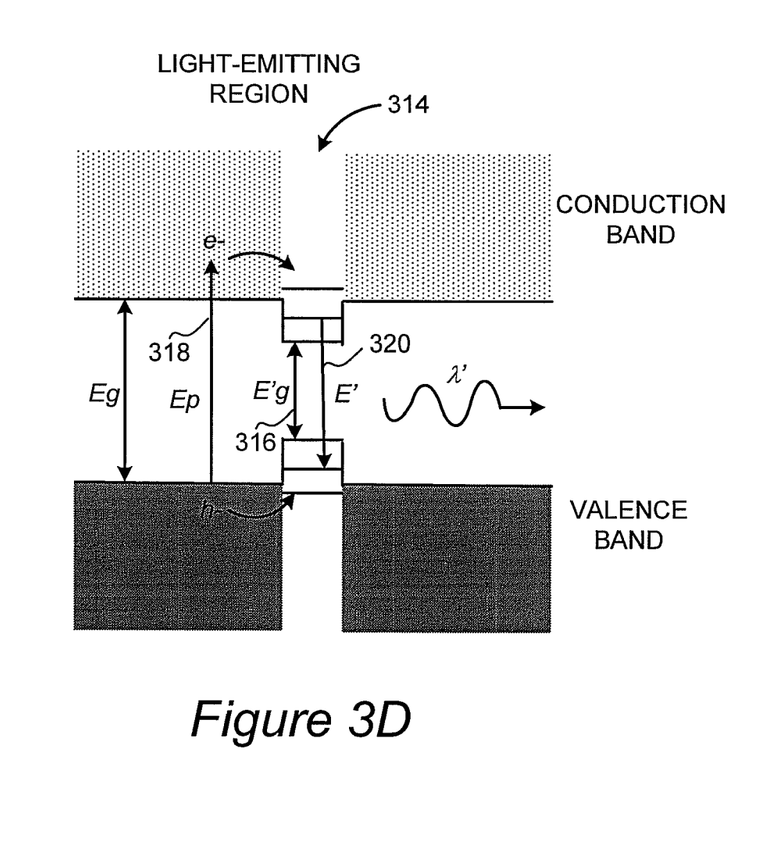
FIG. 3D shows an exemplary electronic energy band diagram associated with a light emitter of a tapered nanowire, according to an embodiment of the invention.

FIG. 3D shows an exemplary electronic energy band diagram associated with a light emitter of a tapered nanowire in accordance with embodiments of the present invention. In FIG. 3D, region 314 represents the quantum states associated with the light emitter, such as the light emitters shown in FIGS. 3A-3C. The light emitter has a smaller electronic band gap, denoted by Eg' 316, than the electronic band gap Eg of the remaining nanowire (i.e., Eg>Eg'). Optically pumping the nanowires with light having photon energy:

$$E_p = \frac{hc}{\lambda_p}$$

where Ep>Eg, excites electrons from near the top of the valence band into electronic energy states in the conduction band. Electrons in the conduction band are free to migrate into the relatively lower energy quantized conduction band states of the light emitter 314, and holes migrate to the relatively higher energy quantized valence band states of the light emitter. As represented in FIG. 3D, electrons in the conduction band of the light emitter 314 spontaneously recombine with holes in the valence band of the light emitter 314 emitting photons of light with Raman excitation wavelengths λ' and corresponding energies E' 320 satisfying:

$$E_p > E' = \frac{hc}{\lambda'} \geq E_g$$

As shown in FIGS. 3A-3C, the light emitted from the light emitters of the nanowires 304, 308 and 312 can be trapped by internal reflection within the nanowires due to the contrast between the refractive index of the nanowire material and the relatively lower refractive index of the surrounding air. In addition, a substantial portion of the emitted light may be reflected off of the reflective layer 103 and directed toward the tip of the nanowire. The Raman excitation light produced by the spontaneous emission and the reflection may also stimulate the emission of more Raman excitation light from the light emitters with the Raman excitation wavelengths λ', and the stimulated emissions further stimulates the emission of even more light with wavelengths λ'. The Raman excitation light can continue to build-up and may constructively interfere to produce amplified light with the Raman excitation wavelengths λ' released near the tip of the nanowires.

Returning to FIGS. 1A-1C, the SERS-active apparatus 100 may be used to identify one or more analyte molecules by selecting the composition of the tapered nanowire or light emitters to emit Raman excitation wavelengths λ' causing the analytes to produce associated Raman spectra of Raman scattered light. Each Raman spectrum can be detected and used to identify each of the analytes. The SERS-active nanoparticles 110 deposited near the tip of the nanowires can be composed of silver ("Ag"), gold ("Au"), copper ("Cu") or another metal suitable for forming a structured metal surface that when illuminated by the Raman excitation wavelengths λ' enhances the intensity of the Raman scattered light.

Figure 4:
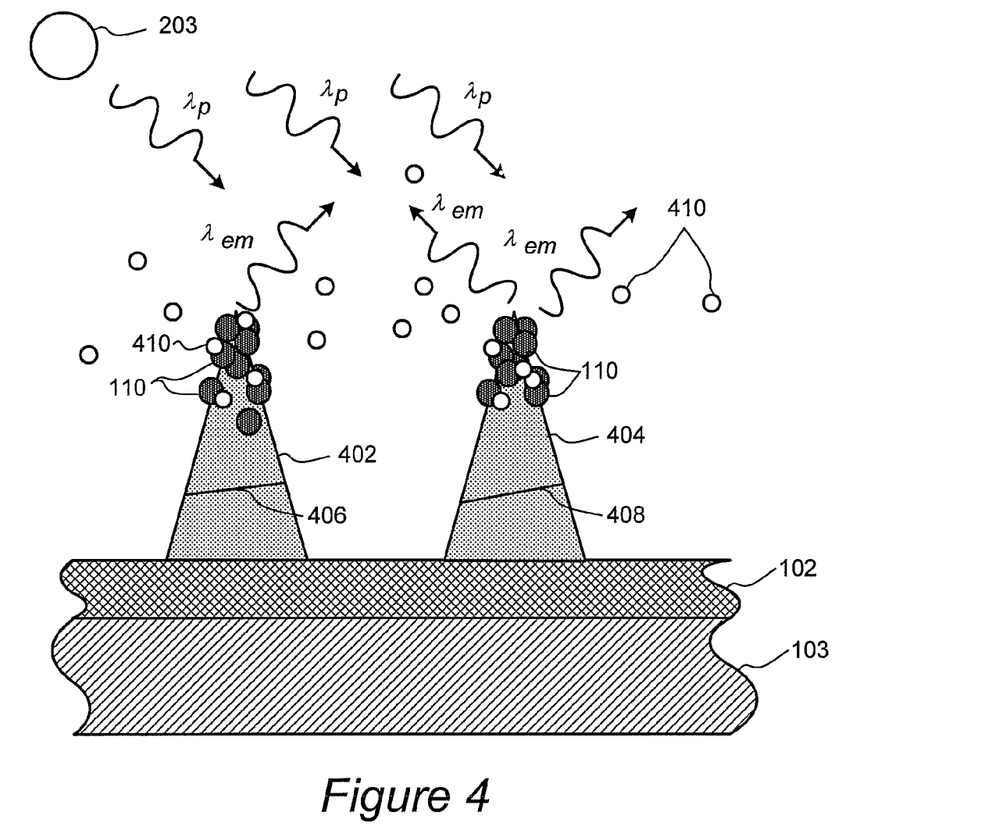
FIG. 4 shows a cross-sectional view of two tapered nanowires of an optically pumped SERS-active system operated to produce a Raman spectrum, according to an embodiment of the invention.

FIG. 4 shows a cross-sectional view of two tapered nanowires 402 and 404 of an optically pumped SERS-active system operated in accordance with embodiments of the present invention to produce a Raman spectrum. The nanowires 402 and 404 are each configured with a single QW layer 406 and 408, respectively, as described above with reference to FIG. 3A. As shown in FIG. 4, an analyte 410 is introduced and the nanowires 402 and 404 are optically pumped with light having a pump wavelength λp that causes the emission of Raman excitation light with Raman excitation wavelengths from the layers 406 and 408. As described above with reference to FIGS. 3A and 3D, the light is substantially confined within, and emitted near the tip of, the nanowires 402 and 404. The Raman excitation wavelengths cause analytes 410 located near the tips of the nanowires 402 and 404 to produce a Raman spectrum of Raman scattered light over a range wavelengths denoted by λem. The intensity of the Raman scattered light may also be enhanced as a result of two mechanisms. The first mechanism is an enhanced electromagnetic field produced at the surface of the SERS-active nanoparticles 110. The materials and thickness of the QWs 406 and 408 can also be selected so that the Raman excitation wavelengths λ' are close to the plasma wavelength of the nanoparticles 110. As a result, conduction electrons in the metal surfaces of the nanoparticles 110 are excited into an extended surface excited electronic state called a "surface Plasmon polariton." Analytes 410 adsorbed on or in close proximity to the nanoparticles 110 experience a relatively strong electromagnetic field. Molecular vibrational modes directed normal to the nanoparticle 110 surfaces are most strongly enhanced. The intensity of the surface plasmon polariton resonance depends on many factors including the wavelength of the Raman excitation light λ' emitted from the QWs 406 and 408 and the morphology of the nanoparticles 110. The second mode of enhancement, charge transfer, may occur as a result of the formation of a charge-transfer complex between the surfaces of the nanoparticles 110 and the analyte 410 absorbed to these surfaces. The electronic transitions of many charge transfer complexes are typically in the visible range of the electromagnetic spectrum.

Note that the SERS-active apparatus 100 may be implemented with any one of the tapered nanowires represented in FIGS. 1A-1C, 2A and 3A-3C and are not limited to nanowires having a single QW layer. In other embodiments, the tapered nanowires can have two or more QW layers.

Figure 5:
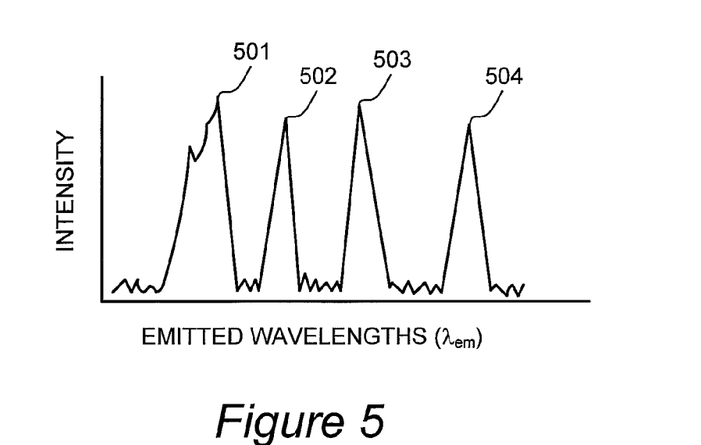
FIG. 5 shows an example Raman spectrum associated with Raman scattered light, according to an embodiment of the invention.

FIG. 5 shows an example Raman spectrum associated with Raman scattered light in accordance with embodiments of the invention. In the example of FIG. 5, the Raman spectrum comprises four intensity peaks 501-504, each peak corresponding to a particular frequency. The intensity peaks 501-504 and associated wavelengths can be used like a finger print to identify the associated analyte.

II. Analyte Sensors and Detectors

Figure 6A:
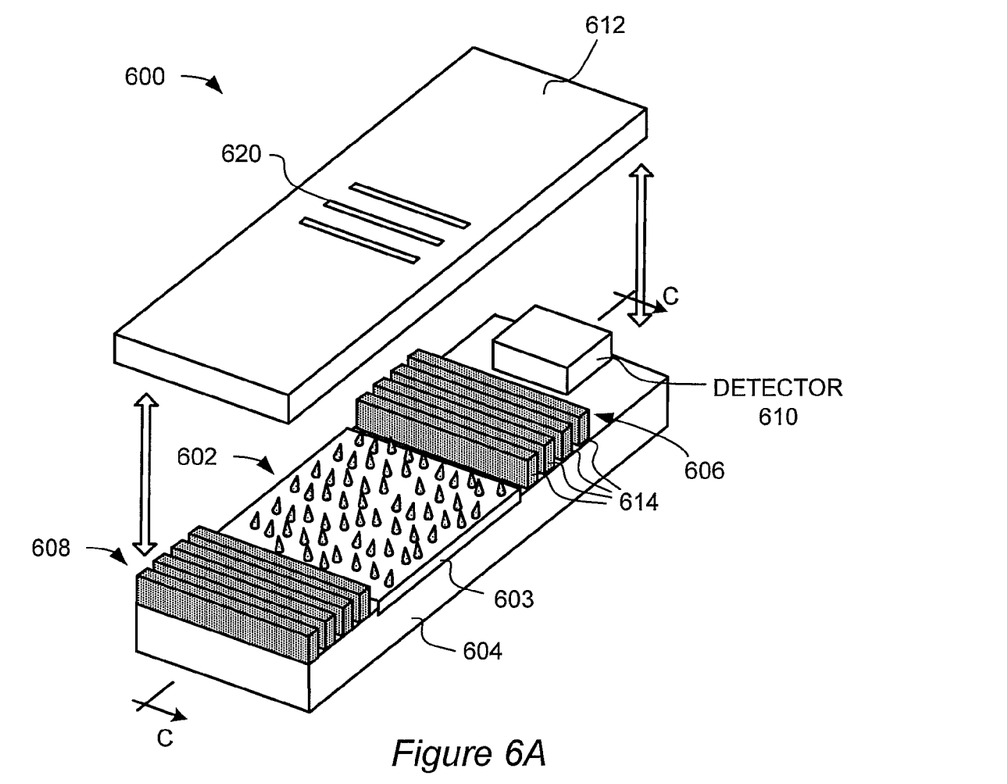
FIG. 6A shows an exploded isometric view and schematic representation of an analyte sensor, according to an embodiment of the invention.

FIG. 6A shows an exploded isometric view and schematic representation of an exemplary analyte sensor 600 configured in accordance with embodiments of the present invention. The sensor 600 includes a SERS-active system 602, which includes a reflective layer 603, embedded in a substrate 604, for instance, as shown in FIGS. 1A and 1B. As shown in FIG. 6A, the SERS-active system 602 is located between a first reflector 606 and a second reflector 608. The sensor 600 also includes a detector 610, such as a photodetector, disposed on the substrate 604 and a cover 612. The SERS-active system 602 may be an optically pumped system, such as the system 100 described above with reference to FIG. 1A.

Figure 6B:
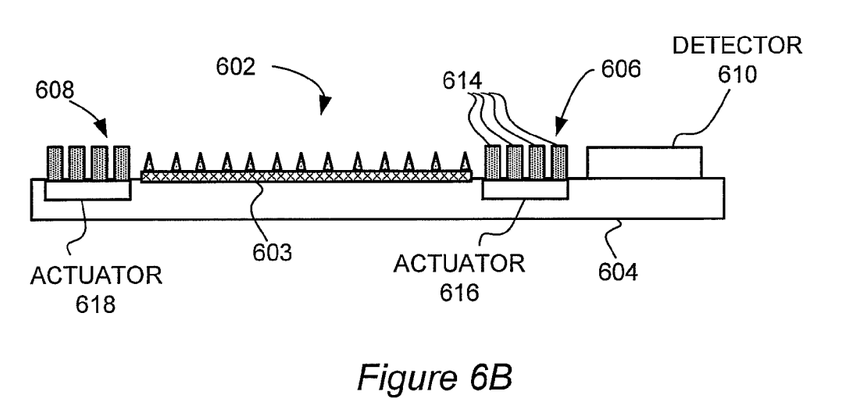
FIG. 6B shows a cross-sectional view of the substrate portion of the sensor along a line C-C, shown in FIG. 6A, according to an embodiment of the invention.

FIG. 6B shows a cross-sectional view of the substrate 604 portion of the sensor 600 along a line C-C, shown in FIG. 6A, in accordance with embodiments of the present invention. As shown in FIG. 6B, the reflectors 606 and 608 are each composed of thin layers of dielectric material separated by air, such as thin layers 614. Appropriate selections of thin layer material, layer thickness, and layer spacing enable the reflectors 606 and 608 to be operated with a specified reflectivity for different wavelengths of light. FIG. 6B also reveals that the reflectors 606 and 608 are mechanically coupled to actuators 616 and 618, respectively. The actuators 616 and 618 may be separately operated to selectively adjust and tune the reflectivity of the reflectors 606 and 608 by controlling the separation distance between the thin layers. The separation distance may be controlled to produce ultra-high reflectivity mirrors of 99% or better over a narrow range of wavelengths, or the reflectors 606 and 608 may be tuned to reflect a broad spectrum of light.

The sensor 600 is operated by introducing an analyte to the nanowires of the SERS-active system 602. This may be accomplished by allowing an analyte in the gas phase to pass through ventilation holes 620 formed in the cover 612, as shown in FIG. 6A. In other embodiments, the analyte may be injected into the region between the SERS-active system 602 and the cover 612. In certain embodiments, when the SERS-active system 602 is configured to be operated as an optically pumped SERS-active system 100, the nanowires are illuminated by light with an appropriate pump wavelength, as described above with reference to FIG. 4. The reflector 608 may be tuned to operate as a nearly fully reflective mirror for the wavelengths of light emitted from the analyte, and the reflector 606 may be tuned to operate a partially reflective mirror for the same wavelengths. As a result, the light emitted from the analyte resonates between the reflector 606 and 608, builds-up, and a portion the light eventually passes through the reflector 606 and is detected by the detector 610.

Figure 7:
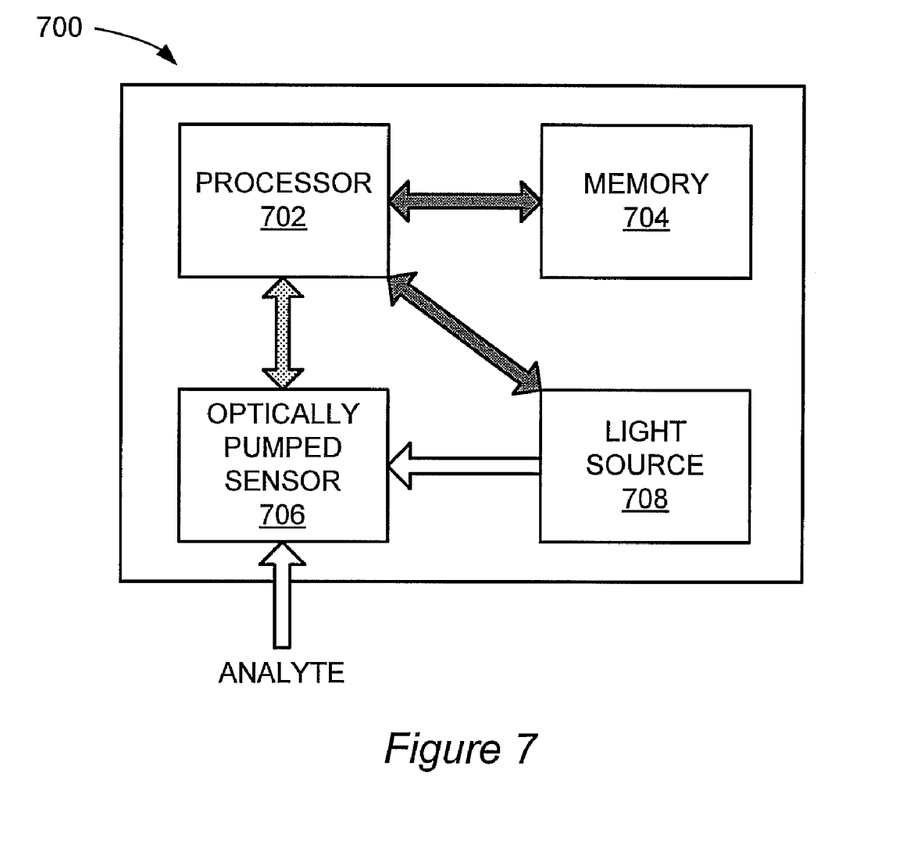
FIG. 7 shows a schematic representation of an analyte detector ASIC, according to an embodiment of the invention.

The sensor 600 may be implemented as a component of an application specific integrated circuit ("ASIC") configured to operate as an analyte detector. FIG. 7 shows a schematic representation of an analyte detector ASIC 700 configured in accordance with embodiments of the present invention. The detector 700 includes a processor 702, memory 704, an optically pumped sensor 706, and a light source 708. The processor 702 is in electronic communication with the memory 704, the sensor 706, and the light source 708. The memory 704 may be flash memory that stores computer readable instructions for operating the light source 708 and stores the information retrieved from the sensor 706. The light source 708 is configured to emit light directed toward to the sensor 706 with wavelengths that pump the nanowires of the sensor 706 as described above with reference to FIG. 4. The processor 702 operates the reflectors of the sensor 706 as described above with reference to FIG. 6, receives the Raman spectra results, and may store the results in memory 704.

Figure 8:
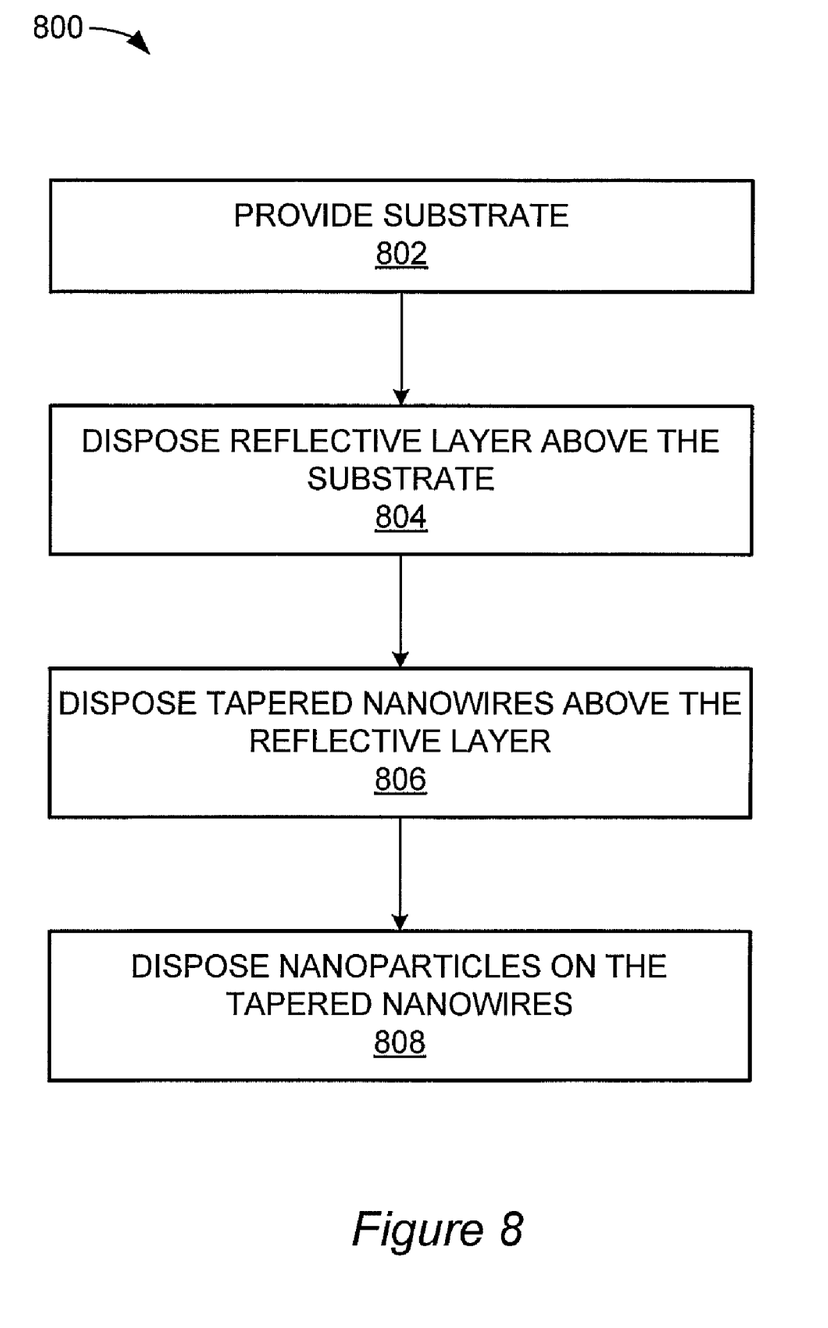
FIG. 8 shows a flow diagram of a method for fabricating an apparatus for performing Surface Enhanced Raman Spectroscopy (SERS), according to an embodiment of the invention.

With reference now to FIG. 8, there is shown a flow diagram of a method 800 for fabricating an apparatus for performing Surface Enhanced Raman Spectroscopy (SERS), in accordance with embodiments of the present invention. It should be understood that the method 800 depicted in FIG. 8 may include additional steps and that some of the steps described herein may be removed and/or modified without departing from a scope of the method 800.

At step 802, a substrate 102 is provided. The substrate 102 may be fabricated in situ or the substrate 102 may comprise a previously fabricated component. In any regard, the substrate 102 may be composed of a dielectric material, including glass, $SiO_2$, $Al_2O_3$, or any other suitable material, such as a metal or semiconductor.

At step 804, a reflective layer 103 is disposed above the substrate 102. The reflective layer 103 is composed of a metallic material or other type of reflective material and may be fabricated to have a mirror-like functionality. In one embodiment, the reflective layer 103, comprises a film of material that is placed on the substrate 102. In another embodiment, the reflective layer 103 is deposited onto the substrate 102, for instance, through physical vapor deposition, chemical vapor deposition, sputtering, etc.

Although steps 802 and 804 have been described as comprising separate steps, steps 802 and 804 may be combined into a single step in one embodiment in which the substrate 102 and the reflective layer 103 are formed of a integrated layer. In this embodiment, the substrate 102 may be fabricated from a reflective material and/or have a surface that has been manipulated to have a mirror-like functionality.

At step 806, a plurality of tapered nanowires 104 are disposed above the reflective layer 103. In one embodiment, the tapered nanowires 104 are disposed directly on a surface of the reflective layer 103, for instance, as shown in FIG. 1B. In another embodiment, the tapered nanowires 104 may be connected to each other through a connecting element 107 and the reflective layer 103 may be provided substantially on the connecting element 107, for instance, as shown in FIG. 1C. In this embodiment, step 804 is performed following step 806.

In accordance with an embodiment, the tapered nanowires 104 are formed using a vapor-liquid-solid ("VLS") chemical synthesis process, which involves depositing particles of a catalyst material such as gold or titanium on a surface of the substrate 102 (FIG. 1C) or the reflective layer 103 (FIG. 1B). The substrate 102 and the reflective layer 103 may be placed in a chamber and heated to temperatures typically ranging between about 250° C. to about 1000° C. Precursor gasses including elements or compounds that will be used to form the nanowires are introduced into the chamber. The particles of the catalyst material cause the precursor gasses to at least partially decompose into their respective elements, some of which are transported on or through the particles of catalyst material and deposited on the underlying surface. As this process continues, nanowires grow with the catalyst particle remaining on the tip or end of the nanowires.

In accordance with other embodiments, the tapered nanowires 104 are formed using a Bosch etching process of Si or similar anisotropic etching of other material (but not limited to) such as quartz, a nanoimprinting process, a combination of etching and nanoimprinting, by physical vapor deposition, by surface atom migration, or etched back by reactive etching with or without a lithographically defined masking pattern.

At step 808, SERs-active nanoparticles 110 are disposed on the tapered nanowires 104. The nanoparticles 110 may be disposed on the tips of the tapered nanowires 104 or throughout the tapered nanowires 104. In accordance with an embodiment, the SERs-active nanoparticles 110 are deposited onto the tapered nanowires 110 through, for instance, PVD, CVD, sputtering, etc., of metallic material, or self-assembly of pre-synthesized nanoparticles.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purposes of illustration and description. They are not intended to be exhaustive of or to limit the invention to the precise forms disclosed.

Obviously, many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents.

What is claimed is:

1. An apparatus for performing Surface Enhanced Raman Spectroscopy (SERS), said apparatus comprising:
    a substrate;
    a reflective layer that is separate from and disposed above the substrate;
    a plurality of tapered nanowires disposed above the reflective layer, each of the plurality of tapered nanowires having a tapered end directed away from the reflective layer, wherein the reflective layer is positioned between the tapered ends of the plurality of tapered nanowires and the substrate; and
    a plurality of nanoparticles disposed on a plurality of the nanowires, wherein each of the plurality of tapered nanowires is to be illuminated with light of a pump wavelength from a light source and reflected from the reflective layer to cause Raman excitation light to be emitted from the tapered end of the nanowire to interact with the nanoparticles and produce enhanced Raman scattered light from molecules located in close proximity to the nanoparticles.

2. The apparatus according to claim 1, wherein the plurality of tapered nanowires are disposed on a surface of the reflective layer with sufficient spacing between the plurality of tapered nanowires to enable light to be reflected from the reflective layer and directed toward tips of the plurality of tapered nanowires.

3. The apparatus according to claim 1, wherein the reflective layer comprises a reflective material disposed on the substrate and wherein the reflective layer forms a mirrored surface.

4. The apparatus according to claim 1, wherein the plurality of tapered nanowires are disposed on the reflective layer.

5. The apparatus according to claim 1, wherein the plurality of nanowires are connected to each other through a connecting element, and wherein the reflective layer comprises a reflective material disposed on the connecting element between the plurality of nanowires.

6. The apparatus according to claim 1, wherein each of said plurality of tapered nanowires has a shape that is selected from a list consisting essentially of: substantially cone-shaped, hemisphere, pillar, pyramid or amorphous shape.

7. The apparatus according to claim 1, wherein the plurality of tapered nanowires are randomly distributed on said reflective layer.

8. The apparatus according to claim 1, wherein the plurality of tapered nanowires are distributed in a substantially uniform density.

9. The apparatus according to claim 1, wherein the plurality of nanowires further comprises one or more light emitters configured to emit Raman excitation light when illuminated with light of the pump wavelength.

10. The apparatus according to claim 1, wherein the plurality of nanoparticles comprises one or more materials selected from a list consisting essentially of: silver, gold, copper and platinum.

11. An analyte sensor comprising:
    an apparatus for performing Surface Enhanced Raman Spectroscopy (SERS), said apparatus comprising,
        a reflective layer;
        a plurality of tapered nanowires disposed above the reflective layer, each of the plurality of tapered nanowires having a tapered end directed away from the reflective layer; and
        a plurality of nanoparticles disposed on a plurality of the nanowires, wherein each of the plurality of nanowires is configured to be illuminated with light of a pump wavelength from a light source and reflected from the reflective layer to cause Raman excitation light to be emitted from the tapered end of the nanowire to interact with the nanoparticles and produce enhanced Raman scattered light from molecules located in close proximity to the nanoparticles;
    a first reflector disposed adjacent to the apparatus and configured to partially reflect Raman scattered light emitted from analyte introduced to the apparatus;
    a second reflector disposed adjacent to the apparatus opposite the first reflector and configured to reflect the Raman scattered light; and
    a photodetector positioned to detect the Raman scattered light transmitted through the first reflector, wherein the Raman scattered light corresponds to a Raman spectrum associated with the analyte.

12. The analyte sensor according to claim 11, further comprising:
    a first actuator mechanically coupled to the first reflector and a second actuator mechanically coupled to the second reflector, wherein the first actuator is to control the reflectivity of the first reflector and the second actuator is to control the reflectivity of the second reflector.

13. The analyte sensor according to claim 11, further comprising:
    a cover for covering the apparatus, said cover comprising at least one opening to enable introduction of the analyte onto the plurality of nanowires.

14. The analyte sensor according to claim 11, wherein the apparatus further comprises a substrate, and wherein the reflective layer comprises a reflective material disposed on the substrate.

15. The analyte sensor according to claim 11, wherein the plurality of nanoparticles comprises one or more materials selected from a list consisting essentially of: silver, gold, copper and platinum.

16. A method for fabricating an apparatus for performing Surface Enhanced Raman Spectroscopy (SERS), said method comprising:
    providing a substrate;
    providing a reflective layer above the substrate, wherein the reflective layer comprises a layer that is separate from the substrate;
    disposing a plurality of tapered nanowires above the reflective layer, each of the plurality of tapered nanowires having a tapered end directed away from the reflective layer, wherein the reflective layer is positioned between the tapered ends of the plurality of tapered nanowires and the substrate; and
    disposing a plurality of nanoparticles on a plurality of the nanowires, wherein each of the plurality of nanowires is configured to be illuminated with light of a pump wavelength from a light source and reflected from the reflective layer to cause Raman excitation light to be emitted from the tapered end of the nanowire to interact with the nanoparticles and produce enhanced Raman scattered light from molecules located in close proximity to the nanoparticles.

17. The method according to claim 16, wherein providing the reflective layer further comprises depositing the reflective layer onto a surface of the substrate.

18. The method according to claim 16, wherein disposing the plurality of tapered nanowires above the reflective layer further comprises employing nano-imprint lithography to form the plurality of tapered nanowires in a material positioned on a surface of the reflective layer.

19. The method according to claim 16, wherein disposing the plurality of tapered nanowires above the reflective layer further comprises employing an etching process to form the plurality of tapered nanowires in a material positioned on a surface of the reflective material.

20. The method according to claim 16, wherein disposing the plurality of tapered nanowires above the reflective layer further comprises disposing the plurality of tapered nanowires on a surface of the reflective layer with sufficient spacing between the plurality of tapered nanowires to enable light to be reflected from the reflective layer and directed toward tips of the plurality of tapered nanowires.

* * * * *